(12) United States Patent
Baudonnet et al.

(10) Patent No.: US 8,309,121 B2
(45) Date of Patent: Nov. 13, 2012

(54) DERMATOLOGICAL COMPOSITIONS COMPRISING AVERMECTIN NANOCAPSULES

(75) Inventors: Lara Baudonnet, Fontenilles (FR); Claire Mallard, Mougins (FR)

(73) Assignee: Galderma S.A., Cham (CH)

( * ) Notice: Subject to any disclaimer, the term of this patent is extended or adjusted under 35 U.S.C. 154(b) by 284 days.

(21) Appl. No.: 12/385,533

(22) Filed: Apr. 10, 2009

(65) Prior Publication Data

US 2009/0258065 A1 Oct. 15, 2009

Related U.S. Application Data

(63) Continuation of application No. PCT/FR2007/052138, filed on Oct. 12, 2007.

(30) Foreign Application Priority Data

Oct. 12, 2006 (FR) ..................................... 06 54237

(51) Int. Cl.
- *A61K 9/48* (2006.01)
- *A61K 31/35* (2006.01)
- *A01N 43/16* (2006.01)

(52) U.S. Cl. ......... 424/452; 514/453; 514/859; 977/809

(58) Field of Classification Search ........................ None
See application file for complete search history.

(56) References Cited

U.S. PATENT DOCUMENTS

| | | | |
|---|---|---|---|
| 4,336,274 A * | 6/1982 | Ross et al. | 426/643 |
| 6,375,960 B1 | 4/2002 | Simonnet et al. | |
| 2003/0152635 A1* | 8/2003 | Heurtault et al. | 424/490 |
| 2005/0048088 A1 | 3/2005 | Zulli et al. | |
| 2005/0079131 A1* | 4/2005 | Lanza et al. | 424/1.11 |
| 2005/0208083 A1 | 9/2005 | Annis | |
| 2006/0100165 A1* | 5/2006 | Manetta et al. | 514/28 |

FOREIGN PATENT DOCUMENTS

| | | |
|---|---|---|
| EP | 1 016 453 A1 | 7/2000 |
| FR | 2 805 761 A1 | 9/2001 |
| WO | WO 00/74489 A | 12/2000 |
| WO | WO 2004/093886 A1 | 11/2004 |
| WO | WO 2005/027872 A2 | 3/2005 |

OTHER PUBLICATIONS

F Bassissi, A Lespine, M Alvinerie. "Assessment of a liposomal formulation of ivermectin in rabbit after a single subcutaneous administration." Parisitol Res., vol. 98, 2006, pp. 244-249, Published online Dec. 10, 2005.*
M Uner. "Preparation, characterization and physico-chemical properties of Solid Lipid Nanoparticles (SLN) and Nanostructured Lipid Carriers (NLC): Their benefits as colloidal drug carrier systems." Pharmazie, vol. 61, 2006, pp. 375-386.*
CAS Registry Record for 816-94-4 (DSPC). 3 pages. Entered STN Nov. 16, 1984.*
M Uner. Pubmed PMID: 16724531.1 printed page. May 2006.*
F Yarrow, TJH Vlugt, JPJM van der Eerden, MME Snel. "Melting of a DPPC lipidbilayer observedwith atomic force microscopy andcomputer simulation." Journal of Crystal Growth, vol. 275, 2005, pp. e1417-e1421.*
Dictionary.com reference for "Syrup." http://dictionary.reference.com/browse/syrup, Accessed Feb. 7, 2012, 3 printed pages.*
Database WPI Week 200377 "Nanoemulsion Cosmetic Composition for Skin Whitening, Containing 5,15-Diacetyl-3-Benzoyllathyrol" Derwent Publication Ltd. 2003 XP002433269.
Database WPI Week 200455 "Ivermectin Water Suspension Nano Capsule Preparation" Derwent Publication Ltd. 2004 XP002433270.
International Search Report PCT/FR2007/052138 dated Mar. 28, 2008.
Shaw et al. "Preformulation Stability screening of ivermectin with non-ionic emulsion excipients", *Pharmazie*, 1999, vol. 54, issue 5, pp. 372-376.

* cited by examiner

*Primary Examiner* — Frederick Krass
*Assistant Examiner* — Isaac Shomer
(74) *Attorney, Agent, or Firm* — SNR Denton US LLP

(57) ABSTRACT

Compositions and nanoemulsions containing lipid nanocapsules dispersed in a hydrophilic phase, such nanocapsules including at least one avermectin compound, are useful for the treatment of dermatological pathologies, e.g., rosacea.

21 Claims, No Drawings

DERMATOLOGICAL COMPOSITIONS COMPRISING AVERMECTIN NANOCAPSULES

CROSS-REFERENCE TO EARLIER APPLICATIONS

This application is a continuation of PCT/FR2007/052138, filed Oct. 12, 2007, and designating the United States (published in the French language on Apr. 17, 2008, as WO 2008/043973 Al; the title and abstract were also published in English), which claims priority under 35 U.S.C. §119 of application Ser. No. 06/54237, filed in France on Oct. 12, 2006, each earlier application hereby expressly incorporated by reference in its entirety and each assigned to the assignee hereof.

BACKGROUND OF THE INVENTION

1. Technical Field of the Invention

The present invention relates to pharmaceutical, in particular, dermatological compositions based on a compound of the avermectin family in the form of a nanoemulsion comprising oily nanocapsules dispersed in an aqueous phase. This invention also relates to a method for the preparation thereof and to its formulation into medicaments useful for the treatment of dermatological conditions/afflictions, in particular of rosacea.

2. Description of Background and/or Related and/or Prior Art

Ivermectin is a mixture of two compounds belonging to the avermectin class, 5-O-demethyl-22,23-dihydroavermectin $A_{1a}$ and 5-O-demethyl-22,23-dihydroavermectin $A_{1b}$. They are also known under the trademark of 22,23-dihydroavermectin $B_{1a}$ and 22,23-dihydroavermectin $B_{1b}$. Ivermectin contains at least 80% of 22,23-dihydroavermectin $B_{1a}$ and less than 20% of 22,23-dihydroavermectin $B_{1b}$. This active agent forms part of the avermectin class, a group of macrocyclic lactones produced by the bacterium *Streptomyces avermitilis* (Reynolds JEF (Ed) (1993) Martindale, The extra pharmacopoeia, 29th Edition, Pharmaceutical Press, London). Avermectins include in particular ivermectin, invermectin, avermectin, abamectin, doramectin, eprinomectin and selamectin.

Ivermectin is more particularly an antihelminthic. It has already been described in humans in the treatment of Onchocerca volvulus onchocerciasis, gastrointestinal strongyloidiasis (anguillulosis) (product Stromectol®), human sarcoptic scabies (Meinking T L et al., *N. Engl. J. Med.,* 1995 Jul. 6; 333(1):26-30 The treatment of scabies with ivermectin) and in the treatment of diagnosed or suspected microfilaremia in subjects suffering from lymphatic filariasis caused by *Wuchereria bancrofti*.

Ivermectin exhibits great instability in the presence of water, and it is particularly difficult to obtain stable pharmaceutical compositions containing it. Indeed, this active ingredient has a very low solubility in water (0.005 mg/ml) and is degraded in a hydrophilic medium. This sensitivity to aqueous media can therefore lead to chemical instability of the active agent and/or to crystallization of the active agent initially solubilized, and limits its formulation in cosmetic or dermatological compositions applied by the topical or oral route.

U.S. Pat. No. 4,389,397 describes the efforts carried out to increase the solubility of ivermectin in an aqueous medium, and in particular proposes solubilizing ivermectin in a mixture of surfactant and organic cosolvents.

Moreover, other concepts have been advanced, such as the solubilization of the active ingredient in a fatty phase (see FR0603452) to improve the stability of this active agent.

However, to prevent the degradation of ivermectin in an aqueous formulation for skin application, it appears advantageous to manipulate the structure of the interface from the ivermectin solubilizing medium and the aqueous phase.

CN 1491551 presents formulations of the ivermectin nanocapsule type in suspension in water produced via polymeric emulsions, that is to say, a solvent-free process employing an in situ polymerization of monomer.

Likewise, FR 2,805,761 describes lipid nanocapsules containing phosphatidylcholines in combination with a hydrophilic cosurfactant derived from polyethylene glycol, Solutol HS 15. However, the presence of a cosurfactant is necessary for the production of the nanocapsules. Moreover, the process for preparing such nanocapsules is carried out by phase inversion (PIT process), which results in the use of temperature cycles in this process. Finally, the active agents are solubilized in an oil composed of medium-chain triglycerides of caprylic and capric acids, which is marketed under the trademark Labrafac WL1349 by GATTEFOSSE.

SUMMARY OF THE INVENTION

It has now surprisingly been discovered that compositions in the form of nanoemulsions comprising ivermectin solubilized in the dispersed oily phase make it possible to chemically stabilize this active agent, and are easy to prepare. Such nanoemulsions comprise ivermectin in solubilized form in a hydrophilic environment, do not require the use of a polymer or an organic solvent, and ensure the chemical stability of the active agent. They can also promote skin penetration by ivermectin, which is useful in the treatment of dermatological conditions/afflictions, in particular rosacea.

The present invention thus features compositions, in particular pharmaceutical compositions, comprising at least one compound of the avermectin family, such compositions being in the form of a nanoemulsion.

The compounds of the avermectin family are in particular selected from among ivermectin, invermectin, avermectin, abamectin, doramectin, eprinomectin and selamectin, and preferably ivermectin.

The present invention therefore also features compositions exhibiting physical stability and chemical stability of the active agent over time.

The expression "physical stability" according to the invention means a composition exhibiting no change in macroscopic appearance (phase separation, change in visual color and the like) or microscopic appearance (recrystallization of the active agents) after storing at temperatures of 4° C. and 40° C. for 2, 4, 8 and 12 weeks.

The expression "chemical stability" according to the invention means a composition in which the content of active ingredient remains stable after three months at room temperature and at 40° C. A stable content of active ingredient means according to the invention that the content exhibits very little variation compared with the initial content, that is to say, that the variation in the content of active ingredient at time T should not be less than 90% to more particularly 95% of the initial content at T0.

The compositions according to the invention comprise from 0.01 to 10% of at least one avermectin by weight relative to the total weight of the composition. Preferably, the compositions according to the invention contain from 0.1 to 5% of at least one avermectin, preferably ivermectin.

The expression "nanoemulsion" means a colloidal lipid system comprising lipid nanocapsules with a solid or semi-solid interface, which are dispersed in a continuous hydrophilic phase, the said nanocapsules containing an oily inner phase in which the avermectin is solubilized, and an envelope forming the semisolid or solid interface from the oily inner phase and the continuous hydrophilic phase.

In particular, the present invention features nanoemulsions prepared with no organic solvent.

DETAILED DESCRIPTION OF BEST MODE AND SPECIFIC/PREFERRED EMBODIMENTS OF THE INVENTION

According to the present invention, the compositions comprise nanocapsules and not nanospheres. The expression "nanocapsules" means particles consisting of a core (inner phase) that is liquid or semiliquid at room temperature, coated with a film (envelope or layer) that is solid at room temperature, in contrast to nanospheres which are matrix particles, that is to say, the entire mass of which is solid. When nanospheres contain a pharmaceutically acceptable active ingredient, the latter is finely dispersed in the solid matrix.

The expression "lipid nanocapsule" means a nanocapsule whose core is composed of one or more fatty substances that are liquid or semiliquid at room temperature, and in which the film (envelope) is of a lipophilic and non-polymeric nature. Indeed, lipid nanocapsules require no polymer and therefore no polymerization in situ.

The expression "room temperature" means a temperature of from 15 to 25° C.

The lipid nanocapsules according to the present invention have a mean size of less than 200 nm, preferably less than 150 nm.

The lipid nanocapsules (simply called "nanocapsules" in the text which follows) are present in the compositions according to the invention in a quantity of from 10 and 30% by weight relative to the total weight of the composition, and preferably from 10 and 20%.

The nanocapsules each consist of a core which is liquid or semiliquid at room temperature, coated with a film which is solid at room temperature.

The film (layer) coating the nanocapsules is the only constituent of the formulation that is solid at room temperature. It is not of a polymeric nature. It is constituted by one or more lipophilic surfactants; advantageously, such lipophilic surfactant(s) is (are) selected from the lecithin family, and preferably the lipophilic surfactant is a hydrogenated lecithin, advantageously in which the percentage of saturated (or hydrogenated) phosphatidylcholine is high. The expression "high percentage" means a quantity of 70 to 99% of saturated (or hydrogenated) phosphatidylcholine relative to the total weight of lecithin. Phosphatidylcholines show good compatibilities with the skin with a very low irritant potential.

As the lecithin used in the present invention is solid at room temperature, this promotes the formation of a semisolid interface in the nanoemulsion.

As lecithins which can be used, exemplary are, in particular, natural or synthetic soybean or egg lecithins having a hydrogenated phosphatidylcholine content greater than 70%, such as for example LIPOID of the S75-3, S100-3 or SPC-3 grade, Epikuron of the 200 SH or 100H grade, or Phospholipon of the 80H, 90H or 100H grade.

The lipophilic surfactant film coating the nanocapsules as defined above is present in a quantity of from 0.1 to 10% by weight, preferably from 1 to 5% by weight relative to the total weight of the composition.

The film of lipophilic surfactant, in particular of lecithin, according to the invention allows on its own the encapsulation of avermectin, preferably ivermectin, which avoids contact from this avermectin and the hydrophilic phase, and thus ensures the chemical stability of this active agent. In particular, the composition, and in particular the film, contains no cosurfactant apart from the lecithins, and in particular no hydrophilic cosurfactant.

Avermectin is thus solubilized in the core of the nanocapsules (inner phase), the said core being liquid or semiliquid at room temperature.

Several preformulation studies ("Preformulation stability screening of ivermectin with non-ionic emulsion excipient" N.O. Shaw, M.M. de Villiers and A.P. Lötter in Pharmazie 54 (1999) pp372-376) have shown that ivermectin is incompatible with certain lipophilic excipients. The analytical results presented in this publication show a degradation of ivermectin in particular in ceteareth-25, ceteareth-6, PEG-8-distearate, PEG-8-stearate, PEG-660-OH-stearate, PEG-4000, polyoxyethylene-10, glycerol monostearate S/E, propylene glycol dicaprylate, cetearyl octanoate, polyglycerol-3-diolate, a mixture of C18-C36 triglycerides, Gamma cyclodextrin, soybean lecithin, cholesterol and stearic acid.

In particular, in this publication, soybean lecithin is mentioned as one of the excipients which can degrade ivermectin. Now, in the present invention, the lecithins used are preferably hydrogenated lecithins. As the studies carried out in Example 1 show, surprisingly, such hydrogenated lecithins do not degrade ivermectin.

The composition of the inner phase (core which is liquid or semiliquid at room temperature) is therefore essential for the stability of the active ingredient. It has been shown, in particular in Example 1, that when the core is essentially constituted by a particular fatty substance which is liquid or semiliquid at room temperature and in which avermectin is solubilized, the stability of the active agent is maintained. Such a fatty substance is in particular diisopropyl adipate, marketed under the trademark Crodamol DA by Croda, or under the trademark Ceraphyl 230 by ISP, or under the trademark Wickenol 116 by Alzo, PPG 15 stearyl ether marketed under the trademark Arlamol E by Uniqema, octyl dodecanol marketed under the trademark Eutanol G by Cognis, C12-C15 alkyl benzoate marketed under the trademark Tegosoft TN by Degussa, dicaprylyl ether marketed under the trademark Cetiol OE, octyl palmitate marketed under the trademark Crodamol OP, ethoxydiglycol marketed under the trademark Transcutol HP, lanolin, benzyl benzoate and mixtures thereof.

In addition to this (these) fatty substance(s), the inner phase may also comprise one or more fatty substances which are liquid or semiliquid at room temperature and do not solubilize the active agent, such as in particular triglycerides having from 18 to 36 carbon atoms, cetyl alcohol marketed under the trademark Speziol C16 by Cognis.

Preferably, the fatty substance of the inner phase is solely constituted by diisopropyl adipate.

Such a fatty substance is present in a quantity of from 90 to 99.99% by weight relative to the total weight of the inner phase.

The continuous hydrophilic phase comprises water. This water may be demineralized water, floral water such as cornflower water, or a thermal or natural mineral water, for example selected from Vittel water, water from the Vichy basin, Uriage water, Roche Posay water, Bourboule water, Enghien-les-Bains water, Saint Gervais-les-Bains water, Néris-les-Bains water, Allevard-les-Bains water, Digne water, Maizières water, Neyrac-les-Bains water, Lons-le- Saunier water, Eaux-Bonnes water, Rochefort water, Saint Christau water, Fumades water and Tercis-les-bains water, Avène water or Aix-les-Bains water.

The water may be present in an amount of from 70 to 90% by weight relative to the total weight of the composition, preferably from 80 to 90% by weight.

The hydrophilic phase may also comprise other hydrophilic compounds such as preservatives or humectants.

Among the preservatives which can be used, parabens or phenoxyethanol are particularly exemplary.

Among the humectants which can be used, glycerine is particularly exemplary.

In one of the preferred embodiments according to the invention, the composition may also comprise a gelling agent. This gelling agent is preferably a cellulose derivative selected from among semi-synthetic cellulose gelling agents such as methylcellulose, ethylcellulose, hydroxypropylmethylcellulose, hydroxyethylcellulose, carboxymethylcellulose, hydroxymethylcellulose and hydroxypropylcellulose, taken alone or as a mixture. Hydroxypropylmethylcellulose or hydroxyethylcellulose is preferably used. These compounds are marketed in particular by Dow Chemical under the trademark Methocel® (for example: Methocel® E4M) or by Hercules under the trademark Natrosol® (for example: Natrosol® 250 HHX). The gelling agent may also be selected from natural gums such as gum tragacanth, guar gum, acacia gum, gum arabic, starch and its derivatives, copolymers of polyacrylic acid and methyl methacrylate, carboxyvinyl polymers, polyvinyl pyrrolidones and their derivatives, polyvinyl alcohols, sodium alginate, pectin, dextrin, chitosan, taken alone or as a mixture, polyacrylamides such as the polyacrylamide/C13-14 isoparaffin/laureth-7 mixture such as for example that marketed by SEPPIC under the trademark Sepigel 305 or the acrylamide, AMPS copolymer dispersion 40%/isohexadecane mixture under the trademark Simulgel 600PHA, or the family of modified starches such as Structure Solanace marketed by National Starch or mixtures thereof.

The gelling agent is used in particular at a concentration of from 0.1 to 10% by weight, preferably from 0.1 to 2% by weight.

The presence of a gelling agent in the compositions according to the invention make it possible to improve the physical stability of the composition over time.

The pharmaceutical compositions according to the invention are useful for the treatment of the skin and may be administered by the topical, parenteral or oral route, whether regime or regimen. Preferably, the composition is administered by the topical route.

By the oral route, the pharmaceutical composition may be provided in liquid or pasty form, and more particularly in the form of gelatin capsules, sugar-coated tablets or syrups.

By the parenteral route, the composition may be provided in the form of suspensions for infusion or for injection.

By the topical route, the composition may be provided in liquid or pasty form, and more particularly in the form of creams, milks, ointments, impregnated pads, syndets, wipes, gels, sprays, foams, lotions, sticks, shampoos or cleansing bases.

The composition in nanoemulsion form thus preferably comprises in water, by weight relative to the total weight of the composition:
 a) 0.1 to 5% of lipophilic surfactant which is solid at room temperature, preferably lecithin;
 b) 1 to 20% of a fatty substance which is liquid or semiliquid at room temperature, preferably diisopropyl adipate;
 c) 0.1 to 5% of at least one avermectin, preferably ivermectin;
 d) 0 to 2% of gelling agent, preferably a cellulose derivative.

The pharmaceutical compositions according to the invention may additionally contain inert additives or combinations of these additives, such as:
 preservatives;
 propenetrating agents;
 stabilizing agents;
 moisture-regulating agents;
 pH-regulating agents;
 osmotic pressure-modifying agents;
 UV-A and UV-B screening agents; and
 antioxidants.

Among the propenetrating agents according to the invention, particularly exemplary are propylene glycol, N-methyl-2-pyrrolidone or dimethyl sulfoxide.

Of course, one skilled in this art will be careful to select the optional compound(s) to be added to these compositions such that the advantageous properties intrinsically attached to the present invention are not, or not substantially, impaired by the addition envisaged.

These additives may be present in the composition from 0.001 to 20% by weight relative to the total weight of the composition.

The present invention also features a method for preparing nanoemulsions comprising at least one avermectin, preferably ivermectin. This method involves a High-Pressure Homogenizer (HPH). In particular, the method according to the invention does not use a Phase Inversion Temperature (PIT) (used in particular in FR 2,805,761 and FR 2,840,531) and therefore does not require a cycle or cycles of temperature increase and decrease. Indeed, the method according to the invention is performed in the HPH in the cold state; the HPH therefore does not require successive heating and cooling, and is not thermoregulated.

The method according to the present invention comprises the following steps:
 (i) Solubilization of avermectin in the fatty substance which is liquid or semiliquid at room temperature, so as to obtain the oily phase.
Preferably, ivermectin is solubilized in the fatty substance, for example in Crodamol DA.
 (ii) Mixing of the hydrophilic compounds, so as to obtain the hydrophilic phase.
In particular, the preservative(s) is (are) mixed with water.
The two phases (lipophilic and hydrophilic) are then preferably heated separately to a temperature preferably of about 75° C.
 (iii) Dispersion of the lipophilic surfactant in the oily phase obtained in (i) or in the hydrophilic phase obtained in (ii).
The lipophilic surfactant, in particular lecithin, is dispersed in the hydrophilic phase or in the inner oily phase; for example, Phospholipon 90H is dispersed in the oily phase, while Lipoid S75-3 is dispersed in the aqueous phase.
 (iv) Mixing the oily and hydrophilic phases.
Once both phases reach the temperature, they are mixed with stirring. Once this prehomogenization has been performed, the emulsion is introduced into the High-Pressure Homogenizer (HPH).
 (v) Introduction of the mixture obtained in (iv) into the High-Pressure Homogenizer, so as to obtain a nanoemulsion.

The use of a High-Pressure Homogenizer requires fixing the number of passages through the homogenization chamber and the homogenization pressure. The homogenization process is then applied:

minimum 500 bar up to 1,000 bar of homogenization pressure in the homogenization chamber, from 5 and 10 passages through the homogenization chamber.

During the passages through the homogenization chamber, the nanoemulsion is not heated and the temperature of the HPH system is not controlled.

(vi) Gelling: optionally, addition of a gelling agent to the composition obtained in (v).

When it is present, the nanoemulsion gelling step occurs at the end of the manufacture after the various passages through the HPH, during cooling of the nanoemulsion.

The gelling agent is then added, with sufficient stirring, to a homogeneous dispersion, during cooling of the nanoemulsion. The stirring is maintained for the period required to complete the step of gelling of the system.

The present invention also features formulation of the nanoemulsion into medicaments useful for treating human dermatological conditions/afflictions.

The nanoemulsions according to the invention are particularly useful for the treatment of rosacea, acne vulgaris, seborrhoeic dermatitis, perioral dermatitis, acneform rash, transient acantholytic dermatitis and acne miliaris necrotica.

Administration of the nanoemulsions according to the invention is more particularly intended for the treatment of rosacea.

To further illustrate the present invention and the advantages thereof, the following specific examples are given, it being understood that same are intended only as illustrative and in nowise limitative. In said examples to follow, all parts and percentages are given by weight, unless otherwise indicated.

EXAMPLE 1

Study of Ivermectin Preformulation

There are numerous excipients used in the formulation of emulsions or liposomes which result in degradation of ivermectin. The Table below presents the results of tests of stability and solubility of ivermectin in various excipients:

According to the above Table, it is not possible to use Solutol HS15 in a nanoemulsion containing ivermectin. Indeed, the Table above shows a degradation at 1 month of 28% of ivermectin. Moreover, it seems that ivermectin, on the one hand, is not perfectly stable in Mygliol 812, which corresponds to an oil composed of medium-chain triglycerides of caprylic and capric acids (C8 and C10), and, on the other hand, has a relatively low solubility in this oil.

On the other hand, it appears possible to formulate ivermectin in a nanoemulsion with soybean lecithin (LIPOID S75-3) and diisopropyl adipate (Crodamol DA) to ensure chemical stability of this active agent. The choices of the inner oily phase and of the surfactant to be used are therefore validated.

EXAMPLE 2

Formulations

| Constituents | Formulation 1 | Formulation 2 | Formulation 3 | Formulation 4 |
|---|---|---|---|---|
| Ivermectin | 1.1% | 1.1% | 1% | 1% |
| Crodamol DA | 13.9% | 13.9% | 14% | 14% |
| Phospholipon 90H | | 1.9% | | 1.9% |
| Lipoid S75-3 | 1.9% | | 1.9% | |
| Nipagin N M | 0.2% | 0.2% | 0.2% | 0.2% |
| Gelling agent - for example cellulose derivative: Natrosol 250 HHX | | | 0.5% | 0.5% |
| Water | Qs 100% | Qs 100% | Qs 100% | Qs 100% |

EXAMPLE 3

Method for the Manufacture of the Formulations of Example 2

The method in this example employs a High-Pressure Homogenizer (HPH).

Manufacturing Steps:

Solubilization of Ivermectin:

Ivermectin is solubilized in the oily phase, here in Crodamol DA.

| | Solubility max | T0 | T 1 month | | T 3 months | |
|---|---|---|---|---|---|---|
| | (mg/g) | (mg/g) | Tambient | 40° C. | Tambient | 40° C. |
| Solutol HS15 (PEG-15 hydroxystearate) | 10.8 | 9.8 | 9.4 (95%) | 7.1 (72%) | ND | ND |
| Benzyl alcohol | 32.8 | 9.9 | 9.8 (99%) | 9.7 (98%) | ND | ND |
| Labrasol (PEG-8 caprylic/capric glycerides) | ND | 8.1 | 8.1 (100%) | 7.9 (98%) | 8.1 (100%) | 5.6 (69%) |
| Labrafac Hydro WL1219 (caprylic/capric triglyceride PEG-4 esters) | 70 | 9.0 | 8.5 (95%) | 6.7 (75%) | 6.3 (70%) | 4.2 (47%) |
| Miglyol 812 | 17.9 | 8.7 | 8.3 (95%) | 8.2 (94%) | 8.3 (96%) | 8.4 (96%) |
| Lipoid S75-3 + benzyl alcohol | ND | 9.4 | 9.5 (101%) | 9.5 (101%) | 9.2 (98%) | 9.7 (103%) |
| Ph90H + benzyl alcohol | ND | 9.25 | 9.7 (105%) | 9.5 (103%) | | |
| Crodamol DA | 94.2 | | Stable over 1 month | | | |
| Benzyl benzoate | 44.2 | | ND | | | |

Ph90H: Phospholipon 90H
ND = not determined

2. Preparation of the Hydrophilic Phase:

The preservative is solubilized in water.

3. Dispersion of the Hydrogenated Phosphatidylcholine:

The hydrogenated phosphatidylcholine is dispersed in the hydrophilic phase or in the oily phase according to the content of phosphatidylcholine.

Both phases are heated separately to about 75° C.

4. Mixing of the Phases:

Once both phases reach the temperature, they are mixed with stirring (turrax homogenization 2 minutes at 8000 rpm).

Once this prehomogenization has been performed, the emulsion is introduced into the HPH.

5. High-Pressure Homogenization:

The use of a High-Pressure Homogenizer requires fixing the number of passages through the homogenization chamber and the homogenization pressure.

The homogenization process is then applied:

minimum 500 bar up to 1,000 bar of homogenization pressure in the homogenization chamber, from 5 and 10 passages through the homogenization chamber.

During the passages through the homogenization chamber, the nanoemulsion is not heated and the temperature of the HPH system is not controlled.

6. Gelling:

When it is present, the nanoemulsion gelling step occurs at the end of the manufacture after the various passages through the HPH, during cooling of the nanoemulsion.

The gelling agent is then added, with sufficient stirring, to a homogeneous dispersion, during cooling of the nanoemulsion.

The stirring is maintained for the period required to complete the step of gelling of the system.

EXAMPLE 4

Studies of Stability of the Formulations of Example 2

1—Physical:

Granulometric Analysis: Zetasizer: Nanoseries-Nano-Zs (Malvern)

Two dilutions are used to carry out the granulometric analyses:

1d: 10 µl of the nanoemulsion in 15 ml of filtered distilled water

2d: 1 ml of 1d in 5 ml of distilled water

Formulation 1 (Lipoid S75-3):

| T0 | Size (nm) | | 141 | | | |
|---|---|---|---|---|---|---|
| | CV % | | 5% | | | |
| Temperature stability | | 4° C. | T. ambient | | 40° C. | |
| T 3 months | Size (nm) | 133 | 124 | 442 | 131 | 485 |
| | CV % | 6 | 13 | 20 | 17 | 20 |
| | % by number | 100% | >99% | <1% | >95% | <5% |

CV = Coefficient of Variation

There are two particle size populations which are not always detected during the measurements as a function of the dilutions analyzed. The appearance of the population from 400 and 800 nm is not reproducible. (High CV for dilution 1d and disappearance for dilution 2d).

Formulation 2 (Phospholipon 90H):

| T0 | Size (nm) | | 157 | | | 600 | |
|---|---|---|---|---|---|---|---|
| | CV % | | 6.5 | | | 25 | |
| | % by number | | >95% | | | <5% | |
| Temperature stability | | 4° C. | | T. ambient | | 40° C. | |
| T 1 month | Size (nm) | 150 | 309 | 133 | 650 | 250 | 433 |
| | CV % | 11 | 20 | 9 | 18 | 9 | 15 |
| | % by number | >95% | <5% | >95% | <5% | >95% | <5% |
| T 2 months | Size (nm) | 242 | 479 | 221 | 630 | 159 | 519 |
| | CV % | 11 | 10 | 8 | 10 | 2 | 10 |
| | % by number | >99% | <1% | >99% | <1% | >95% | <5% |

Formulations 3 and 4 with Natrosol 250HHX:

The physical stability of the gelled formulations 3 and 4 is obtained on the basis of microscopic observations at T0, 6 and 9 months at temperatures of 4° C., ambient and 40° C.

Even after 9 months of stability at the 3 temperatures, formulations 3 and 4 exhibit no degradation and show a finer droplet size than the compositions with no gelling agents.

The physical stability of the compositions according to the invention therefore appear to have been improved with the increase in the viscosity of the composition by addition of the gelling agent.

2—Chemical:

Chemical assay of the compositions according to the invention.

Formulation 1 (Lipoid S75-3):

| T0 | mg/g | | 10.92 | |
|---|---|---|---|---|
| | % titre expected | | 102 | |
| | | 4° C. | T. ambient | 40° C. |
| T 1 month | % titre expected | 105 | 104 | 105 |
| T 2 months | % titre expected | 104 | 107 | 106 |
| T 3 months | % titre expected | | 108 | 102 |

This formulation is chemically stable over 3 months for the 3 temperature conditions.

Formulation 3 (Lipoid S75-3+Natrosol):

| T0 | mg/g | | 10.29 | |
|---|---|---|---|---|
| | % titre expected | | 96 | |
| | | 4° C. | T. ambient | 40° C. |
| T 1 month | % titre expected | ND | 103 | 103 |
| T 2 months | % titre expected | 105 | 100 | 101 |
| T 3 months | % titre expected | 98 | 107 | 81 |

This formulation is chemically stable over 3 months for the 3 temperature conditions.

Formulation 2 (Phospholipon 90H):

| T0 | mg/g | | 10.93 | |
| | % titre expected | | 102 | |
| | | 4° C. | T. ambient | 40° C. |
| T 1 month | % titre expected | 99 | 101 | 99 |
| T 2 months | % titre expected | 99 | 99 | 107 |
| T 3 months | % titre expected | 102 | 101 | 104 |

Formulation 4 (Phospholipon 90H+Natrosol):

| T0 | mg/g | | 10.59 | |
| | % titre expected | | 96 | |
| | | 4° C. | Tambient | 40° C. |
| T 5 months | % titre expected | 101 | 96 | 78 |
| T 9 months | % titre expected | 100 | 96 | 61 |

Conclusion:

Ivermectin is chemically stable over 3 months under the 3 temperature conditions: 4° C., room temperature (Tambient) and 40° C., in the nanoemulsions according to the invention.

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A composition comprising lipid nanocapsules, said lipid nanocapsules comprising:
    (a) an oily inner phase consisting of diisopropyl adipate and ivermectin solubilized in said diisopropyl adipate; and
    (b) a surfactant comprising soybean and/or egg lecithin(s) having a hydrogenated phosphatidylcholine content of greater than 70% by weight, said surfactant being lipophilic, solid at room temperature and coating said oily inner phase;
    said lipid nanocapsules being dispersed in a continuous hydrophilic phase;
    said composition being devoid of any surfactant(s) other than said lecithin(s);
    said composition being devoid of any organic solvent(s) other than said diisopropyl adipate;
    said composition being devoid of propenetrating agents;
    said composition being physically stable at 4° C., ambient temperature and 40° C., for a period of two months;
    said ivermectin being chemically stable in said composition at 4° C., ambient temperature and 40° C., for a period of three months.

2. The composition as defined by claim 1, said lecithin(s) comprising from 0.1 to 10% by weight relative to the total weight thereof.

3. The composition as defined by claim 1, comprising, in water, by weight relative to the total weight thereof:
    a) 0.1 to 5% of lecithin(s);
    b) 1 to 20% of diisopropyl adipate;
    c) 0.1 to 5% of ivermectin; and
    d) 0 to 2% of cellulose derivative.

4. The composition as defined by claim 1, formulated for topical administration.

5. The composition as defined by claim 1, said composition being in the form of a nanoemulsion.

6. The composition as defined by claim 1, formulated for oral administration.

7. The composition as defined by claim 4, formulated as a cream, milk, ointment, impregnated pad, syndet, wipe, gel, spray, foam, lotion, stick, shampoo or cleansing base.

8. A composition comprising lipid nanocapsules, said lipid nanocapsules comprising:
    (a) an oily inner phase consisting of diisopropyl adipate and ivermectin solubilized in said diisopropyl adipate; and
    (b) a surfactant comprising soybean and/or egg lecithin(s) having a hydrogenated phosphatidylcholine content of greater than 70% by weight, said surfactant being lipophilic, solid at room temperature and coating said oily inner phase;
    said lipid nanocapsules being dispersed in a continuous hydrophilic phase; and
    said composition further comprising a gelling agent which is a cellulose derivative selected from the group consisting of methylcellulose, ethylcellulose, hydroxypropylmethylcellulose, hydroxyethylcellulose, carboxymethylcellulose, hydroxymethylcellulose and hydroxypropylcellulose, and mixtures thereof;
    said composition being devoid of any surfactant(s) other than said lecithin(s);
    said composition being devoid of any organic solvent(s) other than said diisopropyl adipate;
    said composition being devoid of propenetrating agents;
    said composition being physically stable at 4° C., ambient temperature and 40° C., for a period of nine months;
    said ivermectin being chemically stable in said composition at 4° C., ambient temperature and 40° C., for a period of three months.

9. The composition as defined by claim 8, said lecithin(s) comprising from 0.1 to 10% by weight relative to the total weight thereof.

10. The composition as defined by claim 8, comprising, in water, by weight relative to the total weight thereof:
    (a) 0.1 to 5% of lecithin(s);
    (b) 1 to 20% of diisopropyl adipate;
    (c) 0.1 to 5% of ivermectin; and
    (d) up to 2% of cellulose derivative.

11. The composition as defined by claim 8, formulated for topical administration.

12. The composition as defined by claim 8, formulated for oral administration.

13. The composition as defined by claim 11, formulated as a cream, milk, ointment, impregnated pad, syndet, wipe, gel, spray, foam, lotion, stick, shampoo or cleansing base.

14. The composition as defined by claim 6, formulated as gelatin capsules, sugar-coated tablets or syrups.

15. The composition as defined by claim 12, formulated as gelatin capsules, sugar-coated tablets or syrups.

16. A composition comprising lipid nanocapsules, said lipid nanocapsules comprising:
(a) an oily inner phase consisting of diisopropyl adipate and ivermectin solubilized in said diisopropyl adipate; and
(b) a surfactant comprising soybean and/or egg lecithin(s) having a hydrogenated phosphatidylcholine content of greater than 70% by weight, said surfactant being lipophilic, solid at room temperature and coating said oily inner phase;
said lipid nanocapsules being dispersed in a continuous hydrophilic phase;
said composition being devoid of any surfactant(s) other than said lecithin(s);
said composition being devoid of any organic solvent(s) other than said diisopropyl adipate;
said composition being devoid of propenetrating agents;
said composition being physically and chemically stable at 4° C., ambient temperature and 40° C., for a period of at least two months.

17. A composition comprising lipid nanocapsules, said lipid nanocapsules comprising:
(a) an oily inner phase consisting of diisopropyl adipate and ivermectin solubilized in said diisopropyl adipate; and
(b) a surfactant comprising soybean and/or egg lecithin(s) having a hydrogenated phosphatidylcholine content of greater than 70% by weight, said surfactant being lipophilic, solid at room temperature and coating said oily inner phase;
said lipid nanocapsules being dispersed in a continuous hydrophilic phase; and
said composition further comprising a gelling agent which is a cellulose derivative selected from the group consisting of methylcellulose, ethylcellulose, hydroxypropylmethylcellulose, hydroxyethylcellulose, carboxymethylcellulose, hydroxymethylcellulose and hydroxypropylcellulose, and mixtures thereof;
said composition being devoid of any surfactant(s) other than said lecithin(s);
said composition being devoid of any organic solvent(s) other than said diisopropyl adipate;
said composition being devoid of propenetratinq agents;
said composition being physically and chemically stable at 4° C., ambient temperature and 40° C., for a period of at least three months.

18. A method for the treatment of dermatological conditions/afflictions selected from the group consisting of rosacea, acne vulgaris, seborrhoeic dermatitis, perioral dermatitis, acneform rash, transient acantholytic dermatitis and acne miliaris necrotica, comprising administering to an individual in need of such treatment, an effective amount of the composition as defined by claim 1.

19. The method as defined by claim 18, said dermatological condition/affliction comprising rosacea.

20. A method for preparing the composition as defined by claim 1, comprising the following steps:
(i) solubilizing ivermectin in diisopropyl adipate to obtain the oily phase;
(ii) mixing hydrophilic compounds to obtain the hydrophilic phase;
(iii) dispersing lecithin(s) in the oily phase obtained in (i) or in the hydrophilic phase obtained in (ii);
(iv) mixing the oily phase with the hydrophilic phase;
(v) introducing the mixture obtained in (iv) into a High-Pressure Homogenizer, to obtain a nanoemulsion.

21. The method as defined by claim 20, comprising a step (vi) of adding a gelling agent to the nanoemulsion obtained in (v).

* * * * *